(12) United States Patent
Lin et al.

(10) Patent No.: US 7,271,914 B2
(45) Date of Patent: Sep. 18, 2007

(54) BIOMOLECULAR SENSOR SYSTEM UTILIZING A TRANSVERSE PROPAGATION WAVE OF SURFACE PLASMON RESONANCE (SPR)

(75) Inventors: Chii-Wann Lin, Taipei (TW); Chih Kung Lee, Taipei (TW); Zhi-Hsiang Sung, Keelung (TW); Shiming Lin, Taipei (TW)

(73) Assignee: National Taiwan University (TW)

( * ) Notice: Subject to any disclaimer, the term of this patent is extended or adjusted under 35 U.S.C. 154(b) by 446 days.

(21) Appl. No.: 11/049,085

(22) Filed: Feb. 2, 2005

(65) Prior Publication Data
US 2006/0170925 A1  Aug. 3, 2006

(51) Int. Cl.
*G01N 21/55* (2006.01)
(52) U.S. Cl. ..................... 356/445; 356/317
(58) Field of Classification Search .............. 355/317; 356/445
See application file for complete search history.

(56) References Cited

U.S. PATENT DOCUMENTS

| | | | | |
|---|---|---|---|---|
| 5,640,234 | A * | 6/1997 | Roth et al. ................ | 356/128 |
| 5,986,808 | A * | 11/1999 | Wang ........................ | 359/585 |
| 6,130,751 | A * | 10/2000 | Haginiwa et al. .......... | 356/401 |
| 6,752,963 | B2 * | 6/2004 | Dickopf et al. ............. | 356/445 |
| 6,956,651 | B2 * | 10/2005 | Lackritz et al. ............. | 356/445 |
| 7,084,980 | B2 * | 8/2006 | Jones et al. ................ | 356/445 |
| 2002/0126290 | A1 * | 9/2002 | Naya .......................... | 356/445 |
| 2003/0020672 | A1 * | 1/2003 | Takatori ..................... | 345/32 |
| 2004/0046963 | A1 * | 3/2004 | Lackritz et al. ............. | 356/445 |
| 2004/0165188 | A1 * | 8/2004 | Anafi et al. ................. | 356/445 |
| 2006/0197952 | A1 * | 9/2006 | Chen et al. ................. | 356/445 |
| 2006/0215165 | A1 * | 9/2006 | Melman ..................... | 356/445 |
| 2006/0227328 | A1 * | 10/2006 | Vanwiggeren et al. ...... | 356/445 |

FOREIGN PATENT DOCUMENTS

EP        1473586 A1 * 11/2004

OTHER PUBLICATIONS

G.Borstel and H.J.Falge, "Surface Polariton in Semi-Infinite Crystals." 1978, Springer-Verlag, Applied Physics, 16, 211-223.*

(Continued)

*Primary Examiner*—Gregory J. Toatley, Jr.
*Assistant Examiner*—Scott M Richey
(74) *Attorney, Agent, or Firm*—Schmeiser, Olsen & Watts (57) ABSTRACT

A biomolecular sensor system utilizing a transverse propagation wave of surface plasmon resonance (SPR) is described. The system comprises: a substrate; a dielectric layer, having a groove therein and standing on top of the substrate; a sensing film layer, sitting at the groove; a pair of prism devices, each resting on one side of the groove and both separating a tunable distance. Besides, the sensor system further comprises a light source, a light detector (a frontend of which connecting to a spectrometer and a backend connecting to a differential amplifier) and a channel with a cover forming inside the groove for the acquisition of the reflected light from the prism devices. Since the sensor system is constructed by exploiting the SPR technique on the transverse propagation, a whole contact surface is under detection (parallel detection) which differentiates it from the traditional method of single-area SPR detection. The sensor system is applicable not only for the far-infrared remote sensing with a transverse distance of several centimeters, but further for the biomedical sensing applications in the miniature sizing and high throughput.

15 Claims, 4 Drawing Sheets

OTHER PUBLICATIONS

Mohanty and Kasiviswanathan, "Two-prism setup for surface plasmon resonance studies." 2005, American Institute of Physics, Review of Scientific Instruments, 76, 033103-1-033103-4.*

Hayashi et al., "Observation of Resonant Photon Tunneling in Phontonic Double Barrier Structures." 1999, Optical Review, vol. 6, No. 3, 204-210.*

* cited by examiner

BIOMOLECULAR SENSOR SYSTEM UTILIZING A TRANSVERSE PROPAGATION WAVE OF SURFACE PLASMON RESONANCE (SPR)

FIELD OF THE INVENTION

The present invention relates to a biomolecular sensor system, more particularly to a biomolecular sensor system utilizing a transverse propagation wave of surface plasmon resonance (SPR) for the testing.

BACKGROUND OF THE INVENTION

The most distinctive feature of biosensors resides on combining biological elements as part of the sensing mechanism and connecting to transducers to achieve the function of detecting biological reactions. Since biosensors work together with micro electromechanics system (MEMS), therefore biosensors are also called biomedical chips. In the development of chip related technologies, optical methods generally have higher sensitivity. Among these methods, fluorescence method has been used extensively in biochips. Recently, surface plasmon resonance (SPR) has become an important means for researches due to its virtues of label-free and real-time capabilities.

The SPR phenomenon has been used extensively in the optical method for measuring the near surface and interface characteristics. It was discovered by physicists and used for studying the characteristics of metals and dielectric thin films at an early stage. Then, chemists used it in the researches for metal/gas or metal/solution interface and LB thin film. The SPR sensors demonstrate an instant and highly sensitive biomolecular interaction measurement, and thus are broadly used in biochemical researches. The surface plasmon is activated at a metal or a semiconductor interface by light energy or electric energy, and the effect of the activated surface plasmon can be measured by the change of the intensity of a light when the incident light is projected at a varying angle or measured by the spectrum of a reflection when a broadband light source is inputted. Regardless of selecting to change the angle of incidence or the wavelength of the incident light, the requirements for both thickness and evenness of the metal film are 1 nm. However, no innovative developments regarding the improvement of the sensing theory and the system sensitivity and the integration and the application of micro tunnnels are found.

The surface plasmon resonance sensor (SPR) is a biosensor that uses the optical theory of the SPR as an energy converter. The change of refractive index caused by changing the composition, concentration or constituents of the medium in the environment will be reflected on the change of the SPR resonance angle by the light kinetic energy of the interface. The surface plasmon resonance occurs at the interface of the metallic and dielectric materials, and a coupler and a TM-wave is excited. Both sides of the electric field penetration depth and transverse propagation in the vertical interface are attenuated. If each sensing area of the chip goes through different activation processes, then it can be combined with an antigen (or antibody) after it is fixed with different corresponding antigen (antibody). Theoretically, only the analyzing object with a successful bond will affect the intensity and change of the reflected light, and the matter exceeding the range of the surface plasmon wave will not affect the measured results. Thus, the sensitivity of this method is very high.

Since the SPR phenomenon has been discovered and used for the biomolecular inspections, most SPR sensing areas are probed by a vertical interface of approximately 200 nm deep, but no report related to the SPR transverse propagation nature is found yet. However, the prior art of the metal and semiconductor film inspection includes the measurement to several centimeters (cm) by using the infrared light in 1970, such as the two-prism coupling method developed by Schoenwald et al. which uses a prism to assist coupling and exciting of the surface electromagnetic waves (SEW) and another prism at a certain distance (depending on the wavelength of incident light) decoupling the SEW into a magnetic wave which is finally received and analyzed by detectors. Some others including Goubau, Barker, Bell, Alexander, Ward, etc. have shown that the metallic surface plasmon can propagate a certain distance with the excitation of infrared light or low-frequency electromagnetic waves. Research shows that such SEW could serve as the "probe" of the metal or metal surface film to obtain the conditions of the metal or surface film along the SEW propagation distance, so that the SEW has become a sensitive sensor. Similar concepts have been extended and applied to the semiconductor industry in 2000. Infrared is mainly used to work with the two-prism methods to detect the adhesive situation of organic matters on the surface of silicon wafer and integrate with the multiple total internal reflection (MTIR) and infrared absorption spectrum (IRAS) optical analytical technologies.

Therefore, this invention further discloses a SPR transverse propagation SEW measurement to observe the signal change of the biochip caused by the surface biomolecular combination conditions within the propagation distance along the metal or surface film. Further that, a short wavelength having a collimated incidence of light source is adopted so that the micro fluidic channel can be integrated with the system to provide a more accurate and miniaturized structure design and make it more applicable for the future development of a multiple-channel high-throughput inspection and a highly sensitive portable instrument.

SUMMARY OF THE INVENTION

Therefore, the primary objective of the present invention is to provide a biomolecular sensor system utilizing a transverse propagation wave of surface plasmon resonance, and the sensor does not need to label the molecules to perform a highly sensitive, fast and parallel inspection and a low-cost transverse surface plasmon wave detection system.

To achieve the foregoing objectives, the present invention provides a biomolecular sensor system utilizing a transverse propagation wave of surface plasmon resonance, and the sensor comprises: a substrate; a dielectric layer, having a groove therein and standing on top of the substrate; a sensing film layer, sitting at the groove; a pair of prism devices, each resting on one side of the groove and both separating a tunable distance.

To achieve the foregoing objective, the present invention further comprises a light source and a light detector (the backend of which connects to a spectrometer or differential amplifier) for receiving the reflected light from the prism devices.

To achieve the foregoing objective, the present invention further comprises a channel with a cover forming at the top of the groove of the dielectric layer.

In the biomolelcular sensor having a transverse surface plasmon resonance, two prism devices have a metal film separately on the corresponding sides and a anti-reflection film separately on the inclined surfaces of the two prism devices.

In the foregoing biomolelcular sensor having a transverse surface plasmon resonance, the sensing film is comprised of a metal material such as a gold (Au) film or a gold and a silver (Ag) film.

In the biomolelcular sensor having a transverse surface plasmon resonance in accordance with the present invention, if the wavelength of the incident light is 633 nm~1000 nm and is used for the interface between the gold film and air, the distance between the two prism devices is 9 µm~95 µm; if the wavelength of the incident light is 633 nm~1000 nm and is used for the interface between the gold film and the water solution, the distance between the two prism devices is 3.5 µm~38 µm.

To make it easier for our examiner to understand the objective of the invention, its structure, innovative features, and performance, we use a preferred embodiment together with the attached drawings for the detailed description of the invention.

DETAILED DESCRIPTION OF THE PREFERRED EMBODIMENTS

[Principle of Measurement]

1. Surface Plasma Wave and Evanescent Wave

Metal is a conductor filled with free electrons ($\sim 10^{23}/m^3$) inside. If these electrons are interacted with an appropriate change of electric field, a surface plasmon oscillation will be produced and propagated along the surface (the interface between a metal and a certain dielectric) in the form of a wave, which is a surface plasma wave (SPW and also known as SEW). This phenomenon was discovered by R. W. Wood in the $20^{th}$ Century during his study on the diffraction phenomenon of the optical grating surface of metals.

The abovementioned additional change of electric field must include the p-polarized light (i.e. the TM wave, and the electric field is oscillating in the direction parallel to the incident plane) and is incident into the prism (coupler) at an angle larger than the critical angle. Then, a total reflection occurs, but not all of the energies are reflected because an evanescent field occurs in the direction perpendicular to the interface. The distribution of energy is exponentially decay away from the interface. Such evanescent energy can activate some surface molecular dipoles, and if the angle of incidence of the light equals the surface plasmon resonance angle, these surface dipoles will resonate with the variations of the incident electric field and transmit on the interface by the change of surface charge density. Therefore, the strongest electric field is distributed on the interface. This is called the Surface Plasmon Resonance (SPR) phenomenon.

The SEW is also an evanescent wave, and the maximum value of the electric field occurs at the interface, and the distribution is exponentially decayed away from the interface. The electric fields in the both sides of the interface are distributed asymmetrically, and the electric field in a metal layer is decayed much faster than that in a dielectric layer. The surface plasmon wave is very sensitive to the optical changes of the dielectric layer adjacent to the metal layer. Further, the surface plasmon wave may be dispersed in the form of light radiation (which is related to the thickness of a metal and the roughness of a surface) and may be converted into heat due to absorption (which is related to the imaginary part of the metal dielectric constant).

2. Coupling Conditions of Surface Plasma Resonance

To cope with Maxwell's equation and the boundary conditions, the additional electric field should be able to excite the SPR. In other words, the transverse wave vector $k_x$ of the incident light produces a coupling effect with the SPR wave vector $k_{sp}$, and the angle of incidence of the light and the dielectric constant of the interfaces should satisfy the matching condition, and the equation is given below:

Coupling condition:

$$k_x = \frac{\omega}{c}\sqrt{\varepsilon_p}\sin\theta \text{ matching } k_{sp}\frac{\omega}{c}\sqrt{\frac{\varepsilon_m(\omega)\varepsilon_s(\omega)}{\varepsilon_m(\omega)+\varepsilon_s(\omega)}}$$

(where, c is the speed of light; $\omega$ is the angular frequency of light; $\varepsilon_p$ is the dielectric constant of the prism; $\varepsilon_m$ is the dielectric constant of the metal film; $\varepsilon_s$ is the dielectric constant of the testing object and $\theta$ is the angle of incidence of light.)

It means that the SPW can be excited and created if $k_x=k_{sp}$, and $k_x$ can be found by the wavelength and the angle of incidence of the incident light, and finally the change of dielectric coefficient of the testing object can be detected.

The SPR phenomenon cannot be produced by simply striking light on the surface of a metal film, instead it needs an appropriate excitation by an optical coupler to strengthen the wave vector propagated along the interface. The methods of coupling incident light shall be as following: prism, optical grating and optical waveguide, where the most common one is the prism coupling method due to its simple components and easy installation.

3. Properties and Equations of Surface Plasmon Wave Resonance

Surface Electromagnetic Wave (SEW) properties derived by the theory of electromagnetism:

(1) Existed in metal/dielectric interface: $\tilde{\varepsilon}_1 = \varepsilon'_1 + i\varepsilon''_1$, $\varepsilon_2 = \varepsilon_2$;

(2) InterfaceProperties: $\varepsilon''_1 < |\varepsilon'_1|$, $\varepsilon'_1 < 0$, $|\varepsilon'_1| > \varepsilon_2$;

(3) Distribution of Intensity: Longitudinal exponential attenuation is $\exp(-|k_{zi}||z|)$ and transverse exponential attenuation is $\exp[-2\mathrm{Im}(k_x)x]$;

(4) Longitudinal Propagated Depth: Longitudinal $z=1/|k_{zi}|$ which is also $z_2=\lambda/2\pi*\sqrt{(\varepsilon'_1+\varepsilon_2)/\varepsilon_2^2}$ in the testing dielectric (dielectric constant $z_1=\lambda/2\pi*\sqrt{(\varepsilon'_1+\varepsilon_2)/\varepsilon'_1{}^2}$ in the metal film;

(5) Transverse Propagated Length:

$$L_x = 1/|2\text{Im}(k_x)| = \frac{c}{\omega}\left(\frac{\varepsilon'_1\varepsilon_2}{\varepsilon'_1+\varepsilon_2}\right)^{-3/2}\frac{\varepsilon'^2_1}{\varepsilon''_1};$$

(6) an optical coupler (excited by optical grating, prism, or optical waveguide) is needed;

[The Detailed Description and Technical Characteristics of the Present Invention are described together with the drawings as follows.]

Figure 1:
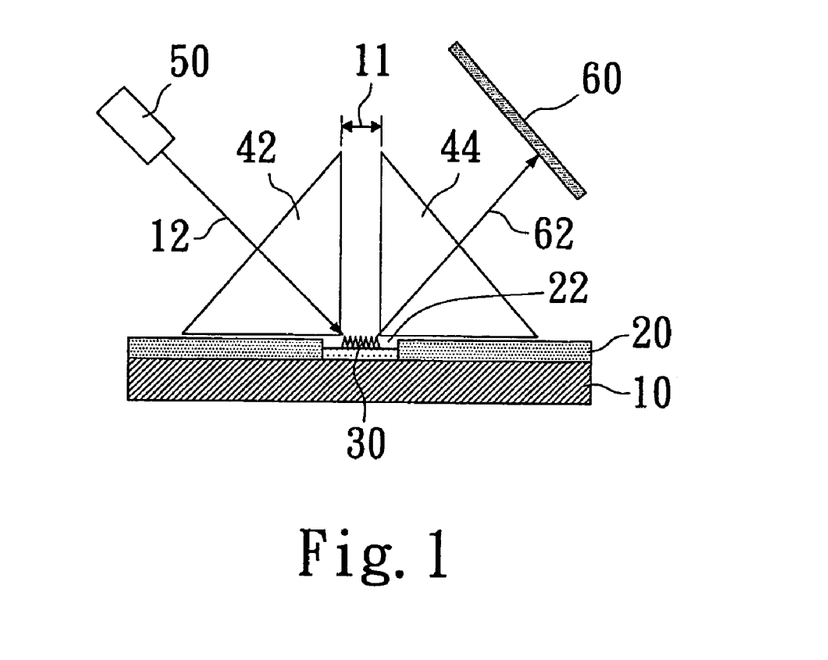
FIG. 1 is a side view of the first embodiment of the present invention.

Please refer to FIG. 1 for the biomolecular sensor system utilizing a transverse propagation wave of surface plasmon resonance (SPR), which comprises a substrate 10; a dielectric layer 20, standing on top of the substrate 10 and having a groove 22 therein; a sensing film layer 30, sitting in groove 22 of the dielectric layer 20; a pair of prism devices 42, 44, each resting on one side of the groove 22 and both separating a tunable distance 11, and the distance between the two prism devices 42, 44 is adjustable.

The invention further comprises a light source 50 for providing an incident light 12 for the prism device 42; and a light detector 60 with its frontend connecting to a spectrometer or a polarizer with a filter and backend connecting to a differential amplifier, etc for receiving a light signal 62 guided out from the prism device 44.

Figure 2A:
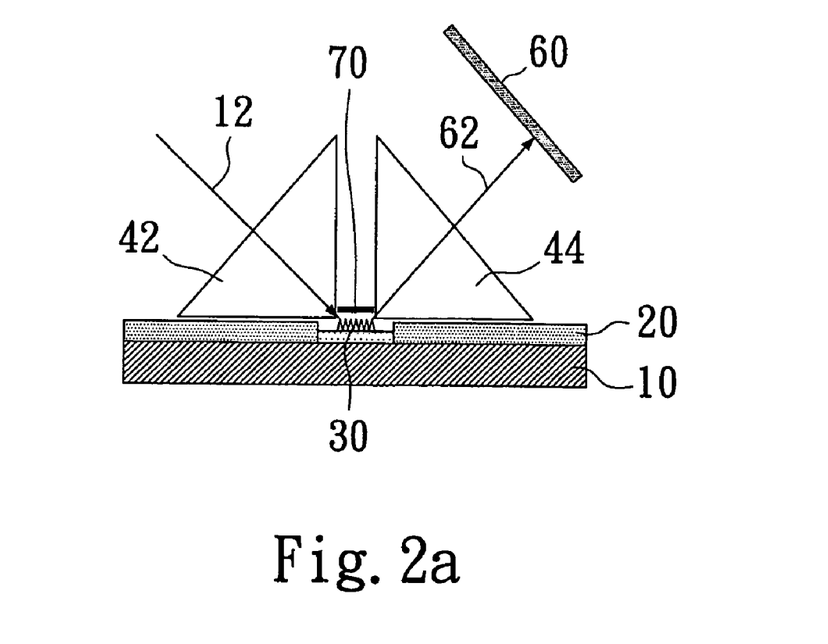
FIG. 2a is a side view of the second embodiment of the present invention.
Figure 2B:
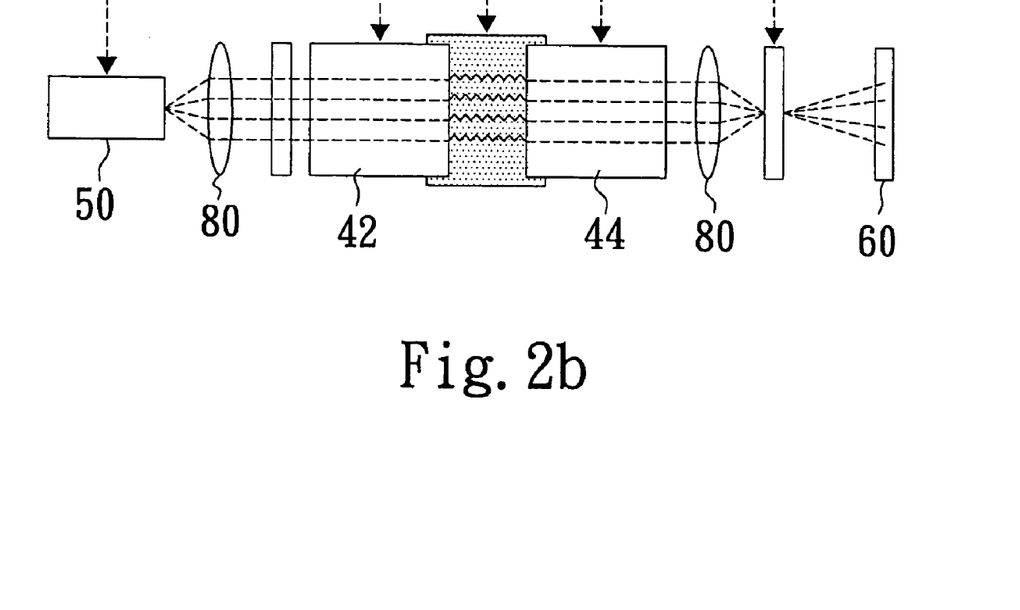
FIG. 2b is a top view of the second embodiment of the present invention.

Please refer to FIGS. 2a and 2b for the side view and the top view of the micro flow design according to the present invention respectively. In FIG. 2a, a cover 70 is included at the top of the sensing film layer 30 and inside the groove of the dielectric layer to become a covered flow design. In FIG. 2b, an appropriate optical device module 80 is disposed individually between the prism device 42 and the light source 50 and between the prism device 44 and the light detector 60 to provide a parallel incident light beam. With the foregoing structure, the sensing film layer 30 can be a SPR sensor chip, and the micro flow design allows the testing fluid containing the testing matter within the range of several tens of μm to improve the actual sensing area as to achieve the very sensitive, multiple-point and parallel light path system design.

The structure above is applied to practical applications in different measuring architectures as shown in FIGS. 4~7.

[Implementation of Optical Measuring Architectures]

1. Attenuated Intensity Measuring Method

The decayed intensity measuring and analyzing method uses a fixed incident wavelength (resonant wavelength) and a refractive index of the sensing film to adjust the angle of incidence of the incident light until SPR occurs (such angle is called SPR angle). Then, the stage is tuned to adjust the transverse distance between a set of prisms, and is moved from the proximity to a farther distance, and a light detector records the intensity of the reflected light for every 1 micron until the intensity approaching 1/e of the initial value, and then the transverse propagated distance is defined by the equation $L_x$ and $$L_x = \frac{c}{\omega}\left(\frac{\varepsilon'_1\varepsilon_2}{\varepsilon'_1+\varepsilon_2}\right)^{-3/2}\frac{\varepsilon'^2_1}{\varepsilon''_1}.$$

Figure 3:
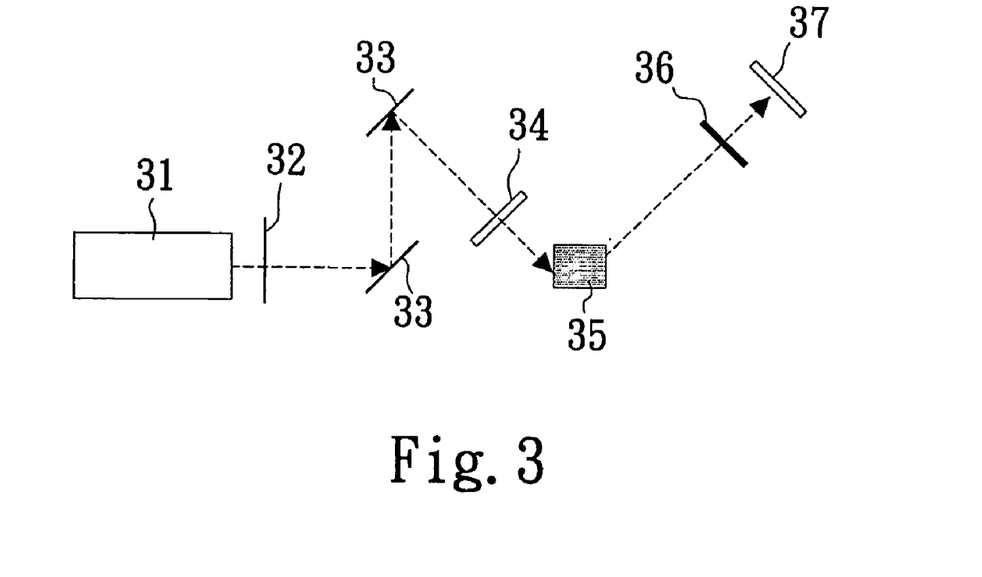
FIG. 3 is a view of the light intensity measuring system that goes with the propagation length according to a preferred embodiment of the invention.
Figure 5:
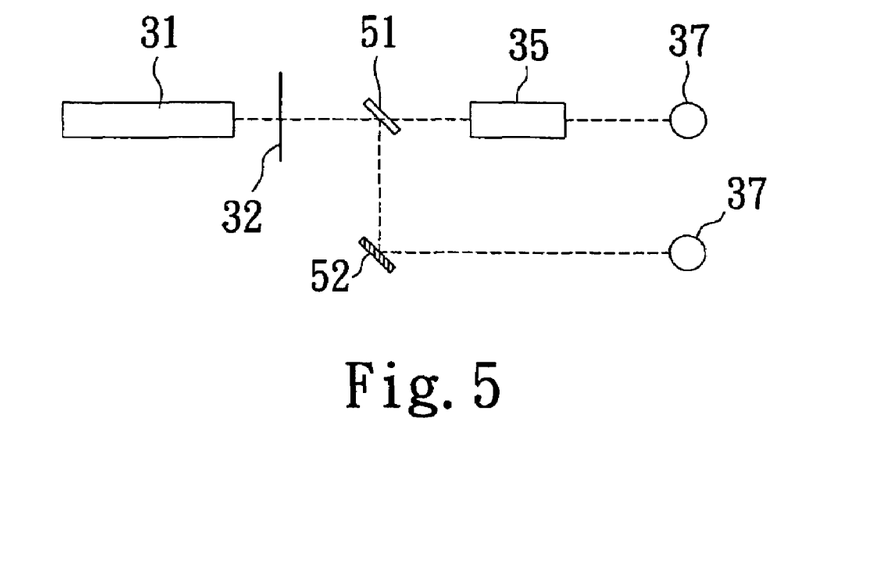
FIG. 5 is a view of the attenuation inspection type SPR system according to a preferred embodiment of the invention.
Figure 6:
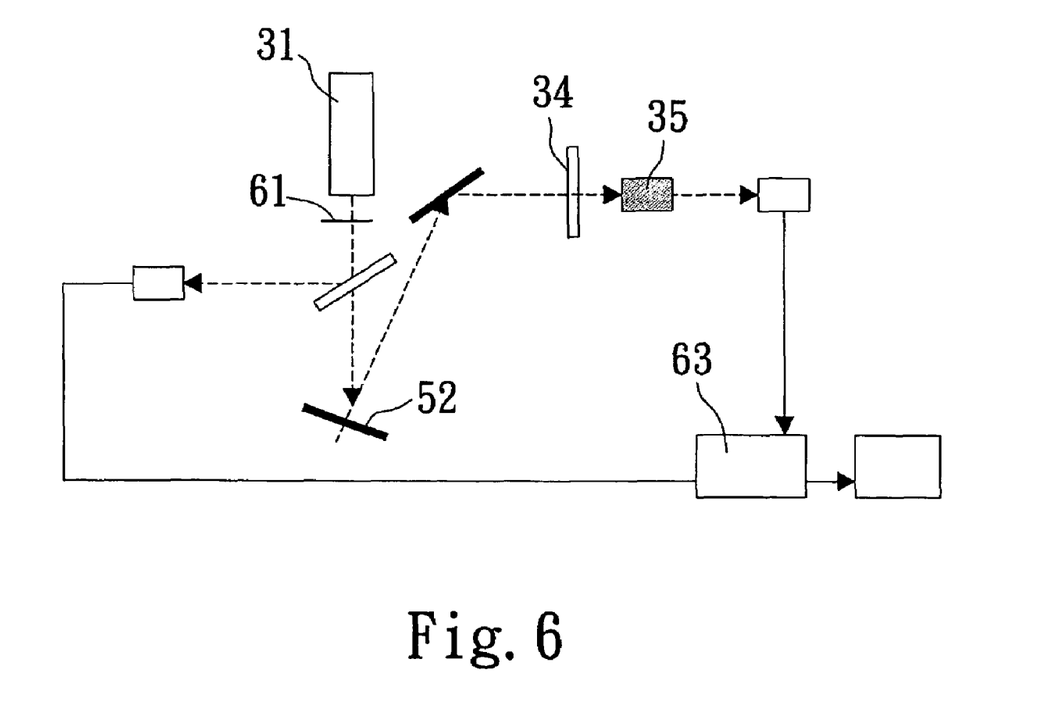
FIG. 6 is a view of the heterodyne inspection type SPR system according to a preferred embodiment of the invention.

The actual change of the refractive index of the dielectric layer can be derived by the above equation. The decayed intensity detection method is an embodiment of controlling the variables. Please refer to FIG. 3 for the light intensity measuring system that goes with the propagation length according to a preferred embodiment of the invention. The light measuring system comprises a light source 31, a ND filter 32, a mirror 33, a polarizer 34, a SPR stage 35, a glass filter 36, and a photo detector 37. The fixed incident wavelength λ of an incident light and the dielectric constant $\varepsilon_1$ of the metal film adjust the angle of incidence θ of the incident light until SPR phenomenon occurs (which is known as SPR angle). Then, a micro positioner is used to adjust the transverse distance between a set of prisms and is moved from the proximity ($L_x=0$) to a farther distance apart, and the intensity of the reflected light is recorded by the photo detector at a distance of every 1 μm until the intensity approaching the initial value (at $L_x=0$) 1/e, and then the transverse propagated distance $L_x$ is defined in the following equation $$L_x = \frac{c}{\omega}\left(\frac{\varepsilon'_1\varepsilon_2}{\varepsilon'_1+\varepsilon_2}\right)^{-3/2}\frac{\varepsilon'^2_1}{\varepsilon''_1}$$

and the change of dielectric constant $\varepsilon_2$ of a known or an unknown dielectric layer can be derived. To cope with the entire light path structure, the appropriate optical devices such as a beam splitter 51 and a mirror 52 to divide the light path into two: (1) Signal Light Path (passing the SPR inspection chip) and (2) Reference Light Path (without passing the SPR inspection chip) as shown in FIG. 5. Finally, the two light rays are compared, and the background noises including any change caused by other lights or ambient temperature are eliminated. Further, the external differential measuring technology can be used to remove the background noises, in addition to the decayed intensity detection analysis. FIG. 6 shows an embodiment which differs from that as shown in FIG. 5 by adding a chopper 61, and a lock-in amplifier 63.

2. Resonant Wavelength Variation Detection and Analysis Method

Figure 4:
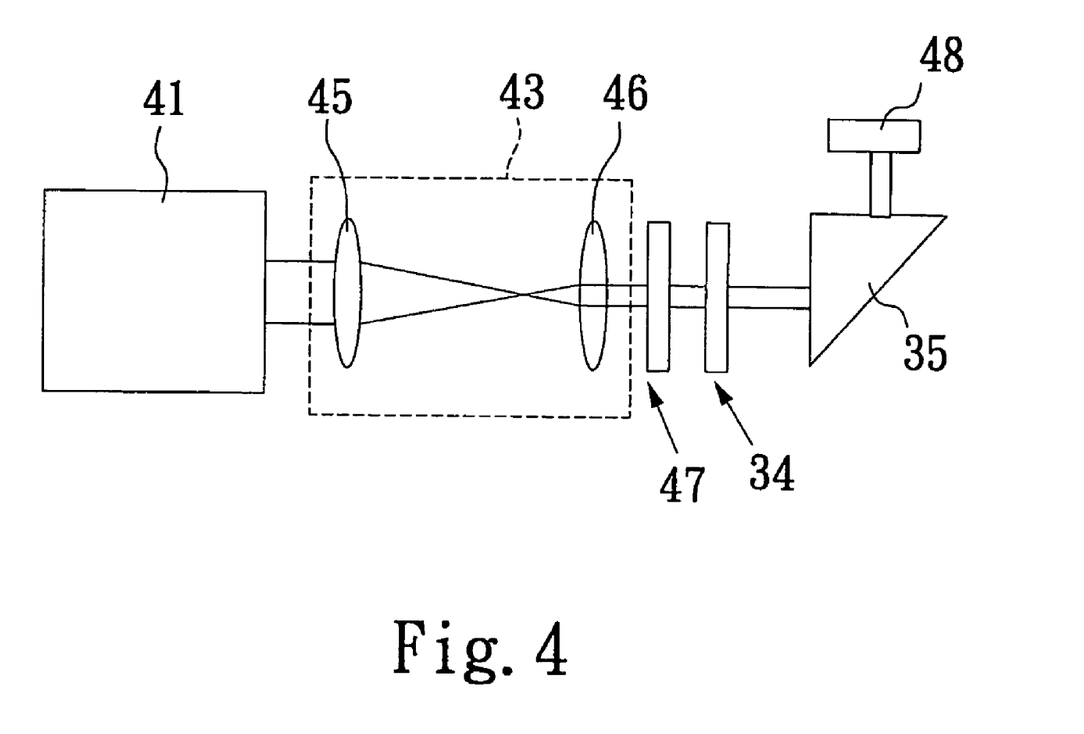
FIG. 4 is a view of the resonance wavelength measuring system that goes with the propagation length according to a preferred embodiment of the invention.

The resonant wavelength variation detection and analysis method uses a fixed transverse propagated length, a white light source, the corresponding value of the refractive index of a known metal film with respect to the change of wavelength to adjust the angle of incidence until the SPR phenomenon occurs (which is the SPR angle). A spectrometer is used to detect the reflected light and observe the wavelength of the absorbed incident light (which is the resonance wavelength), and the equation is used to derive the value of the actual change of the refractive index of the dielectric layer. In other words, the relation is expressed by the equation:

$$\omega = \frac{c}{L_x}\left(\frac{\varepsilon'_1\varepsilon_2}{\varepsilon'_1+\varepsilon_2}\right)^{-3/2}\frac{\varepsilon'^2_1}{\varepsilon''_1},$$

and the embodiment is shown in FIG. 1. However, the micro displacement stage fixes the transverse distance 11 between the two prism devices 42, 44 as shown in FIG. 4, and comprises a white light source 41 and a 4033 lens 45 and a 10x lens 46, adjustable pin hole 47, a polarizer, a SPR stage 35, a photo detector, a spectrometer 48. The fixed transverse propagated length $L_x$, the white light source, and the corresponding value of the dielectric constant $\in_1$ of a known metal with respect to the change of the wavelength are used to adjust the angle of incidence until the SPR phenomenon occurs (which is the SPR angle), and then the spectrometer is used to detect the reflected light and obtain the wavelength of the absorbed incident light (which is the resonant wavelength) by observing the spectrum, and then the equation $$\omega = \frac{c}{L_x}\left(\frac{\varepsilon'_1\varepsilon_2}{\varepsilon'_1+\varepsilon_2}\right)^{-3/2}\frac{\varepsilon'^2_1}{\varepsilon''_1}$$

is used to derive the actual change of the dielectric constant $\in_2$ of the dielectric layer. A spatial filter 43 is comprised of a 40x lens and a 10x lens, such that they have the same focal length and can produce collimated lights with a controllable width. Attention should be paid when using the spectrometer, since the optical fiber detecting head must be parallel to the detecting light and the integral time has to be long enough, or else some wave will not be detected.

The foregoing biomolecular sensor system utilizing a transverse propagation wave of surface plasmon resonance comes with different types of sensing films on the surface of the chip, not limited to the gold film, but also including the more sensitive silver film. Since the activity of the silver film is higher (so that the silver film will be oxidized and affected by the environment). Therefore, in practical applications, it is necessary to coat the silver film first and then the gold film (in the sequence of Au/Ag/glass) Furthermore, the advantages of coating both Ag and Au films include (1) the displacement of the SPR curve is almost the same as that of coating by Au only (it has a larger displacement than that for the Ag coating only); (2) the signal to noise ratio (SNR) is higher than that by coating Au only (falling between that of coating Ag only or coating Au only), (3) the Au coated surface can protect the internal Ag layer, and prevent it from being exposed and oxidized directly. There is another design that adopts a long-range multilayer film concept, which coats upper and lower metal films with other material having similar refractive index in order to improve the transverse propagated distance and the sensitivity of the reaction. The design of using a multilayer film can not only denature the characteristics of the surface of the metal film, but also improve the sensitivity of the detected results.

The foregoing biomolecular sensor system utilizing a transverse propagation wave of surface plasmon resonance has a prism set comprised of an optical lens (BK7 or SF10) or other material having a specific refractive index, and the facing surfaces of the two prism devices are coated with a metal thin film, and the aslant surfaces of the two prism devices have a anti-reflection film.

The angles of the prism can be chosen according to the angle of incidence (such as 45°-45°-90°, 60°-60°-60°, or a special angle design) to facilitate the alignment of the beam. Please refer to FIG. 1 for a preferred embodiment of the invention. The design of the angle of incidence can be adjusted to vertical incidence or aslant incidence according to the material and the angle of the incidence of the prism.

The distance between the prisms $L_x$ is determined by the chosen incident wavelength and the surface of the metal layer. According to the theory of surface plasmon propagation, the equation for the surface plasmon propagation is $$L_x = 1/|2Im(k_x)| = \frac{c}{\omega}\left(\frac{\varepsilon'_1\varepsilon_2}{\varepsilon'_1+\varepsilon_2}\right)^{-3/2}\frac{\varepsilon'^2_1}{\varepsilon''_1}.$$

From the equation, the factors include (1) Resonant Wavelength (2) Transverse Propagated Length (3) Refractive index of Metal Film (Dielectric Constant) and (4) Dielectric Constant of Dielectric material (Dielectric Constant). With the design of the experiment that controls the variables, we can obtain the unknown term of the dielectric refractive index (dielectric constant) directly. In the range of visible light and proximate to the infrared wavelength (633 nm~1000 nm), the range for using in the air is adjusted to 9 μm<$L_x$<95 μm and the range for using in water solution is 3.5 μm<$L_x$<38 μm.

Further, the dielectric layer could be substituted by silicon dioxide ($SiO_2$), ITO, PDMS or other hydrophobic materials. The thickness of this layer can be calculated by Fresnel's equation to obtain the accurate thickness of the gap as in the Otto architecture. For different sensing materials, different types of prisms and different metal films, the independent optimal values can be obtained. If the range of visible light proximate to the infrared with the wavelength 530 nm~1000 nm is used and a 200 nm gold film is used as the sensing film, the range of the thickness of the air gap is 150 nm~1800 nm, and the range of the thickness of the $H_2O$ gap is 80 nm~1100 nm (for BK7 prism) or 90 nm~1120 nm (for SF10 prism). If a 200 nm silver film is used as the sensing layer, then the range of the thickness of the air gap is 600 nm~2300 nm and the range of the thickness of the $H_2O$ gap is 280~1340 nm (for BK7 prism) or 300 nm~13600 nm (for SF10 prism).

Further, the light source is a TM wave falling in a wavelength range from a visible light to a near infrared light 500 nm<$\lambda$<1700 nm entering into the prism to excite the resonance state. The optical inspection method can make use of the decayed intensity (refer to FIG. 3 for the design of this embodiment) or the change of resonance wavelength (refer to FIG. 4 for the design of this embodiment) to go with a photo detector or a spectrometer for the analysis of a single point, an one-dimensional, 2D or 3D intensity inspection. These also can go with the optical architectures as shown in FIGS. 5 and 6 for the analysis of the signals.

The foregoing embodiments are used for example only and are not intended to be a limitation. It is to be understood that the invention is not limited thereto. To the contrary, it is intended to cover various modifications and similar arrangements and procedures, and the scope of the appended claims therefore should be accorded to the broadest interpretation so as to encompass all such modifications and similar arrangements and procedures.

What is claimed is:

1. A biomolecular sensor system utilizing a transverse propagation wave of surface plasmon resonance, comprising:

a substrate;

a dielectric layer, having a groove and standing on top of said substrate;

a sensing film layer, sitting in said groove; and a pair of prism devices, each resting on one side of said groove and both separating a tunable distance.

2. The biomolecular sensor system utilizing the transverse propagation wave of surface plasmon resonance of claim 1 further comprising a light source for providing a light being incident to said prism devices.

3. The biomolecular sensor system utilizing the transverse propagation wave of surface plasmon resonance of claim 1 further comprising a light detector, and a frontend of said light detector connecting selectively to a spectrometer and a backend of said light detector connecting to a differential amplifier for receiving a light signal transmitted from the said prism devices.

4. The biomolecular sensor system utilizing the transverse propagation wave of surface plasmon resonance of claim 1 further comprising a channel with a cover being formed in said groove of said dielectric layer.

5. The biomolecular sensor system utilizing the transverse propagation wave of surface plasmon resonance of claim 1, wherein said two prism devices individually have a metal thin film on the corresponding surfaces of said two prism devices.

6. The biomolecular sensor system utilizing the transverse propagation wave of surface plasmon resonance of claim 1, wherein said two prism devices individually have a reflection-resisting film on the aslant surface of said two prism devices.

7. The biomolecular sensor system utilizing the transverse propagation wave of surface plasmon resonance of claim 1, wherein said two prism devices constitute angles of 45°-45°-90°

8. The biomolecular sensor system utilizing the transverse propagation wave of surface plasmon resonance of claim 1, wherein said two prism devices constitute angles of 60°-60°-60°

9. The biomolecular sensor system utilizing the transverse propagation wave of surface plasmon resonance of claim 1, wherein said two prism devices are maintained selectively at a fixed distance and a variable distance apart; if an decayed intensity measurement is adopted, the distance between said two prism device is variable, and if a resonance wavelength measurement is adopted, the distance between said two prism devices is fixed.

10. The biomolecular sensor system utilizing the transverse propagation wave of surface plasmon resonance of claim 1, wherein said wavelength of an incident light is 633 nm~1000 nm, and if gold film and air interface are adopted, the range of the distance between two prism devices is 9 μm~95 μm and the equation for said transverse propagation wave of surface plasmon resonance is derived from $$L_x = \frac{c}{\omega}\left(\frac{\varepsilon_1'\varepsilon_2}{\varepsilon_1'+\varepsilon_2}\right)^{-3/2}\frac{\varepsilon_1'^2}{\varepsilon_1''}.$$

11. The biomolecular sensor system utilizing the transverse propagation wave of surface plasmon resonance of claim 1, wherein said wavelength of an incident light is 633 nm~1000 nm, and if gold film and water solution interface are adopted, the range of the distance between two prism devices is 3.5 μm~38 μm and the equation for said transverse propagation wave of surface plasmon resonance is derived from $$L_x = \frac{c}{\omega}\left(\frac{\varepsilon_1'\varepsilon_2}{\varepsilon_1'+\varepsilon_2}\right)^{-3/2}\frac{\varepsilon_1'^2}{\varepsilon_1''}.$$

12. The biomolecular sensor system utilizing the transverse propagation wave of surface plasmon resonance of claim 1, wherein said sensing film layer is comprised of a metal material.

13. The biomolecular sensor system utilizing the transverse propagation wave of surface plasmon resonance of claim 1, wherein said sensing film layer is a gold (Au) film.

14. The biomolecular sensor system utilizing the transverse propagation wave of surface plasmon resonance of claim 1, wherein said sensing film layer is comprised of a gold (Au) film and a silver (Ag) film.

15. The biomolecular sensor system utilizing the transverse propagation wave of surface plasmon resonance of claim 13, wherein said sensing film layer is made by depositing a gold (Au) film on top of a silver (Ag) film.

\* \* \* \* \*